United States Patent [19]

Blu et al.

[11] 4,003,243
[45] Jan. 18, 1977

[54] METHOD OF ANALYSIS BY LIQUID-PHASE CHROMATOGRAPHY

[75] Inventors: Gilbert Blu; Flavien Lazarre, both of Pau, France

[73] Assignee: Societe Nationale des Petroles d'Aquitaine, Courbevoie, France

[22] Filed: July 15, 1975

[21] Appl. No.: 596,073

[30] Foreign Application Priority Data

July 18, 1974 France .............................. 74.25036

[52] U.S. Cl. ......................... 73/61.1 C; 210/198 C
[51] Int. Cl.² ........................................ G01N 31/08
[58] Field of Search ............... 73/61.1 C; 210/24 C, 210/198 C

[56] References Cited
UNITED STATES PATENTS

| | | | |
|---|---|---|---|
| 3,373,872 | 3/1968 | Hrdina | 73/61.1 C UX |
| 3,446,057 | 5/1969 | Bakalyar et al. | 73/61.1 C X |
| 3,518,874 | 7/1970 | Hrdina | 73/61.1 C |
| 3,701,609 | 10/1972 | Bailey | 73/61.1 C X |
| 3,847,550 | 11/1974 | Scott et al. | 73/61.1 C X |

Primary Examiner—Richard C. Queisser
Assistant Examiner—Joseph W. Roskos
Attorney, Agent, or Firm—Brisebois & Kruger

[57] ABSTRACT

This invention concerns a method of analysis by liquid-phase chromatography with programmed elution gradient.

According to this method, two chromatography columns, of at least approximately similar porous volume and permeability, are each fed with a mixture of two solvents, in such a way that at any point in time the concentration of one of the solvents at the inlet to the first column is the same as the concentration of the other solvent at the inlet to the second column; the substance for analysis is injected into the inlet of one of the two columns; and the fluids leaving both columns are added to each other to form a mixture for analysis in a concentration detector.

The main purpose of the method is to ensure better analysis of petroleum cuts.

12 Claims, 4 Drawing Figures

METHOD OF ANALYSIS BY LIQUID-PHASE CHROMATOGRAPHY

This invention concerns a method of analysis by liquid-phase chromatography with an elution gradient, giving a response proportional to the concentration of the different eluted solutes.

Methods of liquid-phase chromatographic analysis involving an elution gradient already exist. These involve the use of selective means of detection, unaffected by the components of the eluent, and which give a response proportional to the concentration of one of the solutes and qualitative information on the other solutes.

The method of liquid-phase chromatography using elution gradients offers the best answer to the general problem of elution. In a given chromatographic system, involving a given eluent, or carrier liquid, and a given elute, or solute, because of the spread of values of the coefficient of distribution K, which is the ratio of the concentration of solute in the mobile phase (the carrier liquid) to its concentration in the stationary phase, (the adsorbent in the columns), substances for which K is low are poorly resolved, while resolution of those for which K is high takes excessive time. The effective solution to the general problem of elution consists of changing K for each component during analysis, so that solutes are eluted in minimum time with maximum resolution. This is the "elution gradient" process, in which a carrier liquid consisting of a mixture of two solvents A and B is used, the composition of this mixture being programmed in time according to a concave or convex linear function.

In analytical chromatography, changes in concentration of less than 1 ppm must be detectable. When the composition of the carrier liquid is programmed during elution from 0 to 100 percent, from the point of view of detection, the range of variation of the signal reflecting this composition is approximately $10^6$. This means that an all-purpose concentration detection process cannot be employed, because the range that can be explored by conventional electronics is only around $10^3$, and also because the deviation in concentration caused by the carrier liquid is roughly of the same scale as variations resulting from the passage of elution peaks.

The present process overcomes these difficulties and makes it possible to detect concentrations in liquid-phase chromatography, resolution of the various component substances occurring with approximately the same precision.

According to this new analytical method involving liquid-phase chromatography, with programmed elution gradient, two chromatography columns, of at least approximately similar porous volume and permeability, are each supplied with a mixture of two solvents, in such a way that the concentration of one solvent at the inlet to the first column is the same at any point in time as the concentration of the other solvent at the inlet to the second column, and the product to be analysed is injected into the inlet of one of the two columns and the fluids leaving both columns are added together to form a mixture, which is analysed in a concentration detector.

In this method, differences in porous volume and permeability between the columns are corrected by making the porous volume and permeability of one of the two columns adjustable.

Also in this method, pressure readings are taken at the top of the chromatography columns and, by using the characteristic parameters of a chromatographic system, such as viscosity, compressibility and density of solvents, the value of the signal that should be delivered by the detector in the absence of solute can be worked out at any moment, and this signal compared simultaneously to the signal supplied by the detector.

The apparatus in which this new method of analysis by liquid-phase chromatography is performed comprises two chromatography columns of at least approximately similar porous volume and permeability, each connected by an inlet passage to a metering pump and by an outlet passage to a passage common to both columns, one of the inlet passages containing a nozzle to admit the solute, and the common passage leading to the measuring cell of a concentration detector, each metering pump comprising two cylinders, one containing solvent A and the other solvent B, all four of these cylinders being of equal size, with a piston sliding inside each of them, the piston of one metering pump displacing solvent A and the piston of the other displacing solvent B having parallel axes and being interlocked by means of a beam containing a threaded hole, inside which revolves an endless screw on an axis parallel to the axes of the interlocked pistons and aligned with the shaft of a step-by-step motor, while the two step-by-step motors driving the proportioning pumps for each of the two columns are controlled in such a way that the sum of their speeds is uniform.

In the same embodiment, one of the two columns comprises means of adjusting its porous volume and permeability, for instance by varying the length and/or cross-sectional area of passage.

In one recommended embodiment, the concentration detector is a single all-purpose detector such as a differential refractometer.

In other embodiments, the detector is a single specific detector such as a spectrophotometer using ultra-violet radiation; alternatively, it can comprise an all-purpose detector and a specific detector, one downstream of the other.

In various embodiments, the apparatus comprises, firstly, a comparator, which receives at any time, in digital form, on the one hand the value of any deviation, calculated from the characteristic parameters of the chromatographic system and the pressure measured in the metering pump cylinders, and on the other hand the signal delivered by the concentration detector, and, secondly, a micro-computer which pilots the metering pumps in accordance with the pre-selected elution programme, and supplies the comparator with pressure readings taken in the metering pump cylinders, and, thirdly, means of recording or displaying the value of the difference at any point in time between calculated deviation and the signal supplied by the concentration detector.

In these same embodiments, the porous volumes and permeabilities of the two chromatography columns differ by between 1 and 20 percent.

It will be easier to understand the invention from the following description of possible embodiments, with reference to the accompanying figures.

Figure 1:
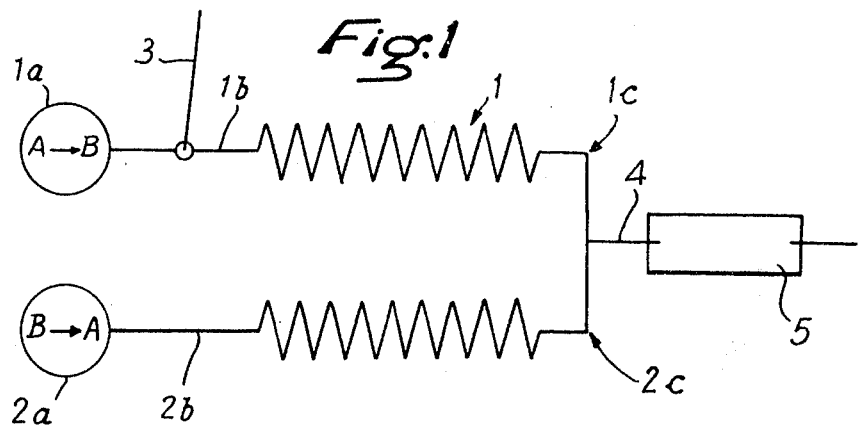
FIG. 1 shows a general diagram.

FIG. 1 shows two chromatography columns of similar size and containing similar filling material. The measuring column 1 is supplied by a metering pump 1a through a passage 1b, and the reference column 2 by a metering pump 2a through a passage 2b.

Figure 2:
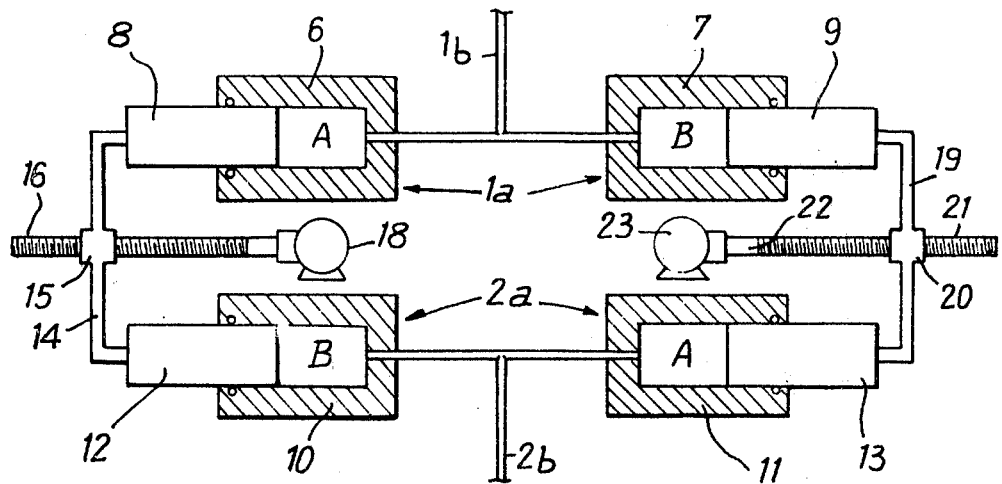
FIG. 2 shows a metering pump with two motors and four cylinders.

Each of these passages 1b and 2b contains an injector for solute, since the functions of the two columns can be reversed. FIG. 2 shows only one injector 3, on passage 1b.

The columns 1 and 2 each have an outlet passage 1c and 2c, opening into a common passage 4, which leads to the measuring cell 5 of the detector.

This detector allows measurement of a parameter related to a universal physical property, such as the refractive index, using a differential refractometer.

FIG. 2 shows how the proportioning pumps 1a and 2a are positioned.

Pump 1a consists of a pair of equal-sized cylinders 6 and 7, with a piston 8 inside cylinder 6 and another piston 9 inside cylinder 7.

Pump 2a consists of a pair of equal-sized cylinders of the same size as cylinders 6 and 7, with a piston 12 inside cylinder 10 and another piston 13 inside cylinder 11.

Pistons 8 and 12, which have parallel axes, are interlocked by means of a beam 14 containing a threaded hole, inside which revolves an endless screw 16, on a parallel axis to the piston axes, and attached to and aligned with the shaft 17 of a step-by-step motor 18.

Pistons 9 and 13, which have parallel axes, are interlocked by means of a beam 19 containing a threaded hole, inside which revolves an endless screw 21, on an axis parallel to the piston axes, and attached to and aligned with the shaft 22 of a step-by-step motor 23.

The apparatus illustrated in FIGS. 1 and 2 functions as follows.

The cylinders 6 and 11 are filled with solvent A and cylinders 7 and 10 with solvent B.

The apparatus is designed in such a way that pistons 8 and 12 discharge equal amounts of solvent, and that equal amounts of solvent are also discharged by pistons 9 and 13.

Since the speeds $V_{18}$ of the motor 18 and $V_{23}$ of the motor 23, programmed as a function of time, are controlled in such a way that their sum is uniformly equal to U (A,B), the amount of solvent A in the mixture of eluents that forms the carrier liquid passing through column 1 is at any point in time the same as the amount of solvent B in the carrier liquid passing through column 2.

In addition, flow-rates at the inlets to columns 1 and 2 are the same: the passage 1b receives a flow proportional to U (A,B) so that $V_{18}(A) + V_{23}(B) = U(A,B)$. In the same way, the passage 2b receives a flow proportional to U (A,B) so that $V_{18}(B) + V_{23}(A) = U(A,B)$. Consequently, the amount $C_A$ (1b) of solvent A at the inlet to passage 1b is equal to:

$$C_A (1b) = V_{18}/U (A,B);$$

and similarly:

$$C_B (2b) = V_{18}/U (A,B);$$

so that the amount of one solvent at the inlet to one column is equal to the amount of the other solvent at the inlet to the other column.

This means that the detector 5 will be supplied with a mixture (A+B) containing 50 percent of each solvent A and B. In theory, the appliance illustrated in FIGS. 1 and 2 can be used to supply an all-purpose concentration detector, since the eluent passing through the detector is uniform, regardless of the elution programme.

In fact, the amounts delivered by the metering pumps to the inlets of columns 1 and 2 is not identical, partly because of the difference in viscosity and compressibility between solvents A and B, and partly because of differences in porosity and permeability between the two columns, which cannot be completely eliminated. Consequently, the signal delivered by the detector is not uniform, but deviates throughout the duration of the elution programme, with a corresponding reduction in the sensitivity of the detector to the solutes.

The table below shows the extent of this deviation for various pairs of solvents, and is based on the following two hypotheses:

maximum pressure (500 bars) in the metering pumps (of length $L_1$);

a column 60 cm long (maximum pressure $P_2$).

The average elution gradient is taken to be 1 percent per minute, the columns are filled with 10-micron particles, and the linear velocity of the binary mixture percolating through the columns is 1 cm per second.

|  | 1 (ppm/h) | $L_1$ cm | 2 (ppm/hr) | $P_2$ bar |
|---|---|---|---|---|
| Pentane/ethyl acetate | 117 | 106 | 209 | 268 |
| Heptane/ethyl acetate | 106 | 106 | 54 | 477 |
| Ethyl acetate/methanol | 57 | 86 | 82 | 388 |
| Methanol/water | 60 | 62 | 62 | 347 |
| Pentane/dioxane | 41 | 40 | 28 | 93 |
| Heptane/dioxane | 56 | 40 | 38 | 255 |
| Dioxane/DMSO | 4.1 | 25 | 1.7 | 267 |
| DMSO/water | 26 | 25 | 11 | 201 |
| Pentane/THF | 217 | 112 | 405 | 283 |

Depending on the degree of precision required, and the pair of eluents chosen, the amount of deviation may or may not be regarded as within the acceptable margin of error.

Figure 3:
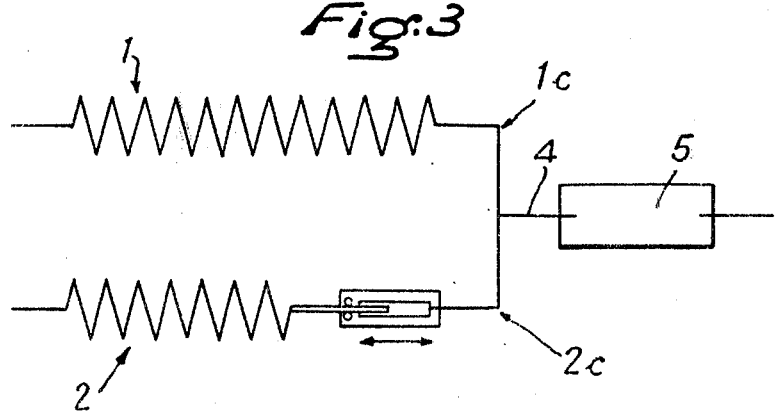
FIG. 3 is a general diagram of an apparatus comprising a gradient-correcting device.

If deviation exceeds this margin, the deviation-correcting device illustrated diagrammatically in FIG. 3 may be used. This figure shows the measuring column 1 with its outlet passage 1c, and the reference column 2 with its outlet passage 2c. To compensate for differences between the two columns, the passage 2c is fitted with a variable-length corrective device; this may consist of a section of telescopic tubing, or an adjustable valve, or a nozzle holder adapted to be fitted with nozzles having different parameters.

This allows a single, overall gradient correction to be effected for one pair of solvents. This correction is the more effective as the gradient is closer to a constant, and as the difference in pressure between column inlets is smaller.

Figure 4:
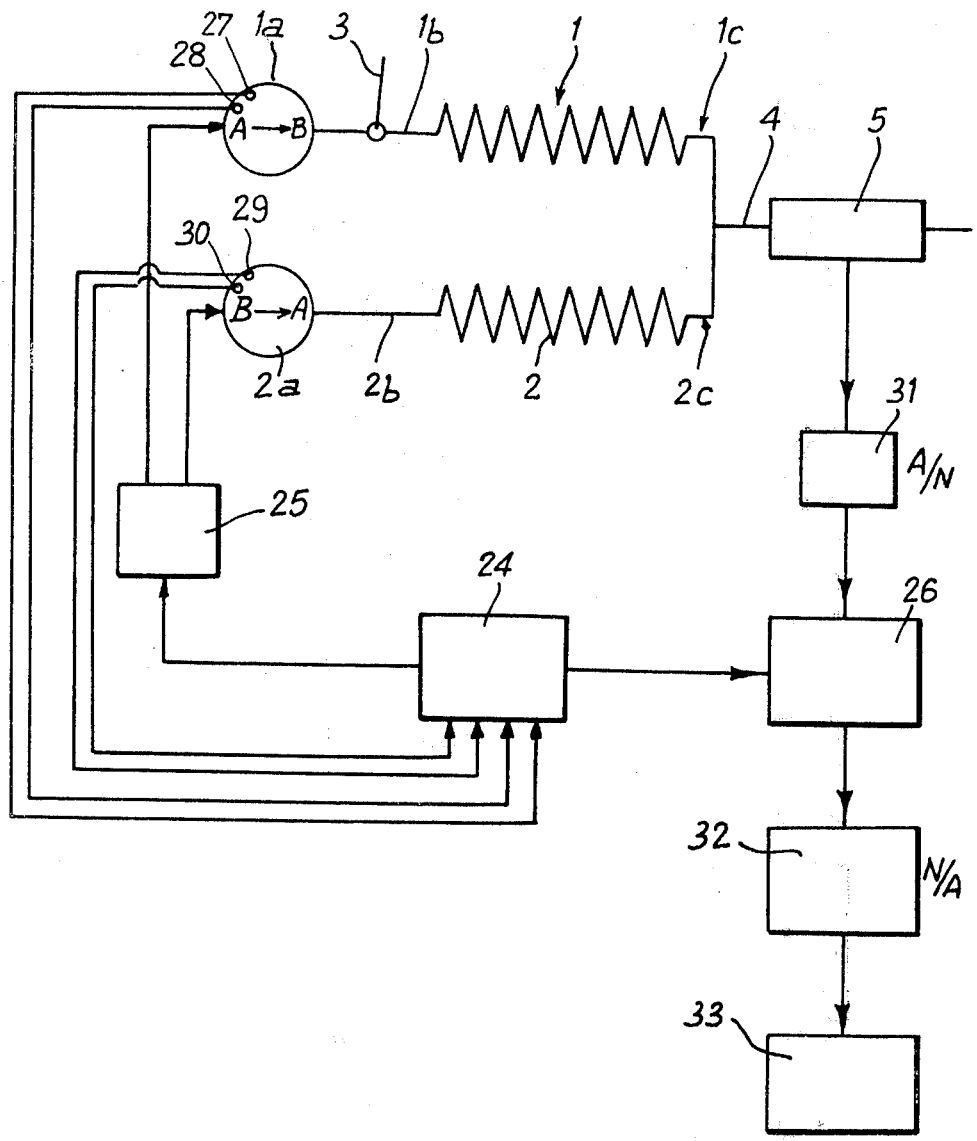
FIG. 4 is a general diagram of an apparatus with deviation compensation by a computer.

If the device illustrated in FIG. 3 does not allow adequate gradient correction, for example where amounts of less than 1 ppm solute have to be detected, a more sophisticated deviation-compensating device, as illustrated in FIG. 4, is necessary.

FIG. 4 includes the items shown in FIG. 1. A pre-programmed micro-computer 24 is connected to the motors 18 and 23 which drive the metering pumps, through an electronic predetermination counter 25, the function of which is to pilot the motors in accordance with the selected elution programme. The micro-computer 24 is also connected to a comparator 26, to which it sends, in digital form, the value of any deviation, at any point in time calculated from the characteristic parameters of the chromatographic system and from the readings of pressure detectors 27, 28, 29 and 30 on the cylinders of the metering pumps 6, 7, 10 and 11.

The comparator simultaneously receives the signal delivered by the detector 5, by means of an A/D converter 31, and calculates the difference, at any point in time, between the calculated deviation and the value of the signal delivered by the detector 5. This difference is transmitted through an digital-analog converter 32 to an analog recorder 33, which allows the results of the chromatographic analysis to be displayed.

The chromatographic apparatus is calibrated in three stages:

1— Zero-setting of the detector

A code, given by a control teleprinter, sets the concentration of solvent at 50 percent. The operator indicates the flow-rate, adjusts zero on the computer, and isolates the reference cell.

2— Testing of differences in porosity between columns

The difference in length between the two parallel columns, which can be between 1 and 20 percent, is adjusted to approximately 10 percent. the corresponding difference in porosity is tested with a 50.01 percent concentration of solvent A for a certain period. This is predetermined in the computer memories.

The operator must check that the detector is delivering a signal of the right kind, with a clear enough definition of a level. If the porous volumes of the two columns are too similar, the level will not be observable on the chromatogram, or will not be clear, and making accurate measurement of its characteristics impossible. In this case, the porous volume of one of the two columns will have to be adjusted to increase the difference. If the signal alternates between positive and negative, the operator must also increase the difference in length between the columns.

Once this has been done, the operator will have the three characteristic parameters of the chromatographic system:

$S$ = value in millivolts of 90 percent of the height of the 50.01 percent concentration (pip);
$\Delta T$ = duration of this pip in seconds;
$T$ = duration in minutes of the saturation cycle of the system of parallel columns.

3— Calibration of the detector

The detector is calibrated automatically by computer, on emission of a selected code, and comprises four phases.

In phase 1, the values S, T and T are stored in the computer memories, the compressibility coefficients XA and XB of solvents A and B, respectively.

The response from the detector is comparable to a second-degree curve, so that calculation of the coefficients of the equation representing the response curve of the detector requires determination of two points on the curve.

This can be done as follows. First, the pistons delivered a 50 percent mixture of solvents, to adjust the detector zero, for a certain length of time, after which the computer emits a signal for a 50.01 percent concentration of solvent A, so that the characteristics of a level can be measured.

The pistons again deliver the 50 percent mixture, resulting in a negative level and measurement of the duration of the saturation cycle.

Emission of a 50.1 percent concentration signal produces a second level.

In this way, two points on the detector response curve are established, and the detector can be calibrated.

Using the equipment described above and the method just mentioned, extremely complex problems and analyses can be handled, such as determining the composition of heavy fractions of petrochemical distillation cuts. In this case, advantage is taken of the fact that liquid-phase chromatography allows an initial qualitative separation into families. Each family, comprising numerous compounds with very similar physical-chemical properties, can be analysed quantitatively by means of an all-purpose concentration detector and elution-gradient device as described above.

This new method of analysis, and apparatuses comprising the main features of the apparatus described and illustrated above, can be used in the analysis of a large number of complex mixtures.

What is claimed is:

1. A method of analysis by liquid-phase chromatography with a pre-selected elution-gradient programme, which comprises the steps of supplying each of two chromatography columns having at least approximately similar porous volumes and permeability, with a mixture of two solvents, while maintaining the concentration of one solvent at the inlet to one column equal at any point in time to the concentration of the other solvent at the inlet to the other column, injecting the product to be analyzed into the inlet of one of the two columns, bringing the fluids leaving both columns together to form a mixture, and analyzing said mixture in a concentration detector.

2. A method as defined in claim 1, which comprises the step of correcting any differences in porous volume and permeability occurring during filling of the columns by adjusting a parameter of one of said columns.

3. A method as defined in claim 1 which comprises the step of taking pressure readings at the top of the chromatography columns, determining the value of the signal delivered by the detector at any moment in the absence of solute by measuring the characteristic parameters of the chromatographic system, and comprising this signal simultaneously to the signal supplied by the detector.

4. An apparatus for performing analysis by liquid-phase chromatography, comprising two chromatography columns of at least approximately similar porous volume and permeability, each connected by an inlet passage to a metering pump and by an outlet passage to a passage common to both columns, a nozzle for admitting solute leading into one of said inlet passages, and a concentration detector having a measuring cell supplied by said common passage, each metering pump comprising two cylinders, one for containing a first solvent and the other for containing a second solvent, all four cylinders being of equal size, a piston sliding in each cylinder, a first motor connected to drive at the same speed the piston in the cylinder of one pump containing the first solvent and the piston in the cylinder of the other pump containing the second solvent, a second motor connected to drive at the same speed the cylinder of the other pump containing the first solvent and the cylinder of said one pump for containing said second solvent, and means for maintaining the sum of the speeds of said two pumps constant.

5. An apparatus as claimed in claim 4 in which one of the two columns comprises means for adjusting its porous volume and permeability.

6. An apparatus as defined in claim 4, wherein the concentration detector is a single all-purpose detector.

7. An apparatus as defined in claim 4, wherein the concentration detector is a single specific detector.

8. An apparatus as defined in claim 4, in which the concentration detector comprises an all-purpose detector and a specific detector, one arranged downstream of the other.

9. An apparatus as defined in claim 4, comprising a comparator, connected to receive at any time, in digital form, on the one hand, the value of any deviation in the signal to be expected from the concentration detector, calculated from the characteristic parameters of the chromatographic system and the pressure measured in the proportioning pump cylinders, and on the other hand, the signal delivered by the concentration detector, a micro-computer connected to control the metering pumps in accordance with a pre-selected elution programme, and supply the comparator with pressure readings taken in the metering pump cylinders, and means for indicating the value of the difference at any point in time, between the calculated deviation and the signal supplied by the concentration detector.

10. An apparatus as defined in claim 9, in which the porous volumes and permeabilities of the two chromatography columns differ by between 1 and 20 percent.

11. Apparatus as claimed in claim 6 in which said concentration detector is a differential refractometer.

12. Apparatus as claimed im claim 7 in which said concentration detector is a spectrophotometer using ultra-violet radiations.

* * * * *